US010203326B2

(12) United States Patent
Fukushima et al.

(10) Patent No.: US 10,203,326 B2
(45) Date of Patent: Feb. 12, 2019

(54) METHOD OF DETECTING TARGET SUBSTANCE

(71) Applicant: FURUKAWA ELECTRIC CO., LTD., Tokyo (JP)

(72) Inventors: Masayuki Fukushima, Tokyo (JP); Michio Ohkubo, Tokyo (JP); Kazutomi Miyoshi, Tokyo (JP); Masataka Nishida, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 208 days.

(21) Appl. No.: 15/088,742

(22) Filed: Apr. 1, 2016

(65) Prior Publication Data
US 2016/0291003 A1 Oct. 6, 2016

Related U.S. Application Data

(63) Continuation of application No. PCT/JP2014/076258, filed on Oct. 1, 2014.

(30) Foreign Application Priority Data

Oct. 2, 2003 (JP) ................................. 2013-207387

(51) Int. Cl.
*G01N 33/543* (2006.01)
*G01N 21/64* (2006.01)
*G01N 33/552* (2006.01)
*G01N 33/58* (2006.01)

(52) U.S. Cl.
CPC ... *G01N 33/54333* (2013.01); *G01N 21/6428* (2013.01); *G01N 33/54326* (2013.01); *G01N 33/54346* (2013.01); *G01N 33/552* (2013.01); *G01N 33/582* (2013.01); *G01N 2021/6439* (2013.01)

(58) Field of Classification Search
CPC ....... G01N 2021/6439; G01N 21/6428; G01N 33/54326; G01N 33/54333; G01N 33/54346; G01N 33/552; G01N 33/582
See application file for complete search history.

(56) References Cited

U.S. PATENT DOCUMENTS

| 2004/0101822 | A1 | 5/2004 | Wiesner et al. | |
|---|---|---|---|---|
| 2006/0263908 | A1* | 11/2006 | Hirai | B82Y 15/00 436/526 |
| 2008/0241964 | A1 | 10/2008 | Kaieda et al. | |
| 2009/0017561 | A1* | 1/2009 | Aizawa | B82Y 15/00 436/514 |
| 2010/0062433 | A1 | 3/2010 | Nagaoka et al. | |
| 2013/0210047 | A1 | 8/2013 | Tang et al. | |
| 2016/0216273 | A1* | 7/2016 | Nishida | G01N 33/54326 |

FOREIGN PATENT DOCUMENTS

| EP | 2009442 A2 | 12/2008 |
|---|---|---|
| EP | 2320437 A1 | 5/2011 |
| EP | 3054297 A1 | 8/2016 |
| JP | 2006-070250 A | 3/2006 |
| JP | 2006-517985 A | 8/2006 |
| JP | 4518767 B2 | 8/2010 |
| WO | WO 2008/001868 A1 | 1/2008 |

OTHER PUBLICATIONS

English translation of Written Opinion of the International Searching Authority, issued in PCT/JP2014/076257, dated Jan. 13, 2015.*
English translation of Written Opinion of the International Searching Authority, issued in PCT/JP2014/076258, dated Jan. 13, 2015.*
Christopher-Stine et al., "A Novel Autoantibody Recognizing 200-kd and 100-kd Proteins Is Associated With an Immune-Mediated Necrotizing Myopathy", Arthritis & Rheumatism, vol. 62, No. 9, Sep. 2010, pp. 2757-2766.
Govindaiah et al., "Synthesis and characterization of poly(styrene-co-fluorescein O-methacrylate)/poly(N-isopropylacrylamide)-$Fe_3O_4$ core/shell composite particles", Polymer, vol. 52, No. 22, Sep. 2011, pp. 5058-5064.
Guo et al., "Poly(N-isopropylacrylamide)-Coated Luminescent/Magnetic Silica Microspheres: Preparation, Characterization, and Biomedical Applications", Chem. Mater., vol. 18, No. 23, 2006, pp. 5554-5562.
International Search Report (PCT/ISA/210) issued in PCT/JP2014/076257, dated Jan. 13, 2015.
International Search Report (PCT/ISA/210) issued in PCT/JP2014/076258, date Jan. 13, 2015.
Office Action issued in Japanese Patent Application No. 2013-207388, dated Mar. 8, 2016.
Written Opinion (PCT/ISA/237) issued in PCT/JP2014/076257, dated Jan. 13, 2015.
Written Opinion (PCT/ISA/237) issued in PCT/JP2014/076258, dated Jan. 13, 2015.

(Continued)

*Primary Examiner* — Galina Yakovleva
(74) *Attorney, Agent, or Firm* — Birch, Stewart, Kolasch & Birch, LLP

(57) ABSTRACT

A method of detecting a target substance, containing the steps of:
  incorporating labeling particles into a test liquid containing an analyte;
  heating the test liquid;
  irradiating the test liquid with excitation light, and
  detecting the target substance contained in the test liquid depending on a state of light emission of the labeling particles;
wherein an aggregation state of the labeling particles is changed by the heating step; and
wherein the labeling particles have a thermoresponsive polymer on a surface of a composite particle containing a magnetic material and a fluorescent material, and further have a biomolecule having properties of binding with the target substance.

6 Claims, 3 Drawing Sheets

(56) References Cited

OTHER PUBLICATIONS

Extended European Search Report for corresponding European Application No, 14850582.9, dated Mar. 20, 2017.
Hoshino et al., "Separation of Murine Neutrophils and Macrophages by Thermoresponsive Magnetic Nanoparticles," Biotechnol. Prog,, vol. 23, No. 6, 2007 (Published on Web Oct. 20, 2007), pp. 1513-1516.
Wang et al., "Poly (N-Isopropylaorylamide)-Coated Multifunctional Nanoparticles for Cell Tracking," Photomedicine and Laser Surgery, vol. 28, No. 2, 2010 (published Apr. 1, 2010), pp. 201-205.

* cited by examiner (1)                              (2)

METHOD OF DETECTING TARGET SUBSTANCE

CROSS-REFERENCE TO RELATED APPLICATIONS

This application is a Continuation of PCT International Application No. PCT/JP2014/076258 filed on Oct. 1, 2014, which claims a priority under 35 U.S.C. § 119 (a) to Japanese Patent Application No. 2013-207387 filed in Japan on Oct. 2, 2013. Each of the above applications is hereby expressly incorporated by reference, in its entirety, into the present application.

TECHNICAL FIELD

The present invention relates to a method of detecting a target substance.

BACKGROUND ART

Fine particles on which various kinds of biological substances are immobilized have been widely utilized in medical diagnosis, a biotechnology research field and the like. Fine particles that are formed of a variety of materials and have various particle diameters, forms and functions have been studied and proposed therein. Among them, there exists a technology in which magnetic particles are utilized. Specific examples include a technology in which magnetic particles on which an antibody is immobilized are used to perform affinity column chromatography. At this time, in latex beads, an antigen is purified by repeating centrifugal separation and washing operation. Therefore, a large amount of solvent is required. On the other hand, when the magnetic particles are used, the complicated operation as described above is not required because particles can be easily separated by means of a magnet. That is, in comparison with the latex beads having no magnetism, the magnetic particles have an advantage of capability of rapidly and simply purifying the antigen. Moreover, the magnetic particles are also adapted to automation using a machine because such centrifugal separation and application of the large amount of solvent become unnecessary. For the above reason, immunological magnetic particles have been frequently utilized as a carrier in immunodiagnosis (sandwich method) in recent years.

In order to improve molecular recognition properties of the magnetic particles, a surface area thereof is preferably increased. In this regard, in order to further increase the surface area per unit volume for magnetic beads, further reduction of a particle diameter is effective. On the other hand, if the particle diameter of the magnetic particles falls in a nanometer order, the magnetism of the particles is significantly weakened. Further, magnetic separation by means of the magnet becomes significantly difficult under the influence of Brownian motion in water. In order to solve this problem, proposals have been made on arts of using particles in which a thermoresponsive polymer is immobilized on a surface layer of magnetic nanoparticles having a particle diameter of several tens of nanometers (see Patent Literatures 1 and 2). A target substance is detected depending on a change of colors (into transparency) of magnetic materials by aggregating thermoresponsive magnetic particles by heating therein. Specifically, absorbance of a reaction liquid over time is monitored by heating the liquid after a reaction with the target substance, and existence of the target substance (analyte) is judged by the absorbance being gradually decreased.

Patent Literature 1: WO 2008/001868 pamphlet
Patent Literature 2: Japanese Patent No. 4518767

SUMMARY OF INVENTION

Technical Problem

It is certain that detection sensitivity thereof is considered to be improved by the above-mentioned thermoresponsive magnetic particles to compensate for the low magnetism caused by micronized particles. However, a further improvement in the detection sensitivity is desired in order to realize a further microanalysis or securely prevent a false negative or a false positive in medical diagnosis.

Therefore, the present invention is contemplated for providing a method of detecting a target substance in which high detection sensitivity can be realized in detection of the target substance utilizing thermoresponsive magnetic particles.

Solution to Problem

The problems are solved by the following means.
[1] A method of detecting a target substance, comprising the steps of:
incorporating labeling particles into a test liquid comprising an analyte;
heating the test liquid;
irradiating the test liquid with excitation light, and
detecting the target substance included in the test liquid depending on a state of light emission of the labeling particles;
wherein an aggregation state of the labeling particles is changed by the heating step; and
wherein the labeling particles have a thermoresponsive polymer on a surface of a composite particle comprising a magnetic material and a fluorescent material, and further have a biomolecule having properties of binding with the target substance.
[2] The method of detecting a target substance as described in the above item [1], wherein non-existence of the target substance is identified by development of fluorescence emission of the labeling particles that are locally gathered in the test liquid after the heating step, and existence of the target substance is identified by no development of the fluorescence emission of the gathered labeling particles.
[3] The method of detecting a target substance as described in the above item [1] or [2], wherein a dispersant is introduced into the test liquid.
[4] The method of detecting a target substance as described in any one of the above items [1] to [3], wherein a wavelength of the excitation light is 300 to 700 nm and a wavelength of the fluorescence is 350 to 800 nm.
[5] The method of detecting a target substance as described in any one of the above items [1] to [4],
wherein the composite particle comprises a phase having the magnetic material and a phase having the fluorescent material, and
wherein the phase having the fluorescent material is constituted of a continuous phase formed of a transparent material and a dispersed phase formed of the fluorescent material.
[6] The method of detecting a target substance as described in any one of the above items [1] to [5], wherein the test liquid is heated so as to span a critical solution temperature (CST) of the thermoresponsive polymer in the range of 10° C. to 100° C.

[7] The method of detecting a target substance as described in any one of the above items [1] to [6], wherein magnetic force is provided for the test liquid and the labeling particles in an aggregated state are gathered in a portion provided with the magnetic force.

[8] The method of detecting a target substance as described in any one of the above items [1] to [7], wherein an average particle diameter of the composite particle is less than 1 μm.

[9] The method of detecting a target substance as described in any one of the above items [5] to [8], wherein the transparent material comprises silica or polystyrene.

[10] The method of detecting a target substance as described in any one of the above items [1] to [9], wherein the magnetic material is magnetite, nickel oxide, ferrite, cobalt iron oxide, barium ferrite, carbon steel, tungsten steel, KS steel, a rare earth cobalt magnet or hematite.

"Having on the surface of particle" means existence in the form of directly contacting with the surface and also existence outward of the surface through a different material.

Advantageous Effects of Invention

The method of detecting a target substance of the present invention realizes high detection sensitivity in detection of a target substance by utilizing thermoresponsive magnetic particles.

Other and further features and advantages of the invention will appear more fully from the following description, appropriately referring to the accompanying drawings.

DESCRIPTION OF EMBODIMENTS

A method of detecting a target substance of the present invention is applied by incorporating specific labeling particles mentioned later into a test liquid containing an analyte, heating the test liquid and then irradiating the test liquid with excitation light, and depending on a state of fluorescence emission of the labeling particles to be emitted at the time. In the following, the present invention is described in detail centering on preferred embodiments thereof.

[Detection Method]

Figure 1:
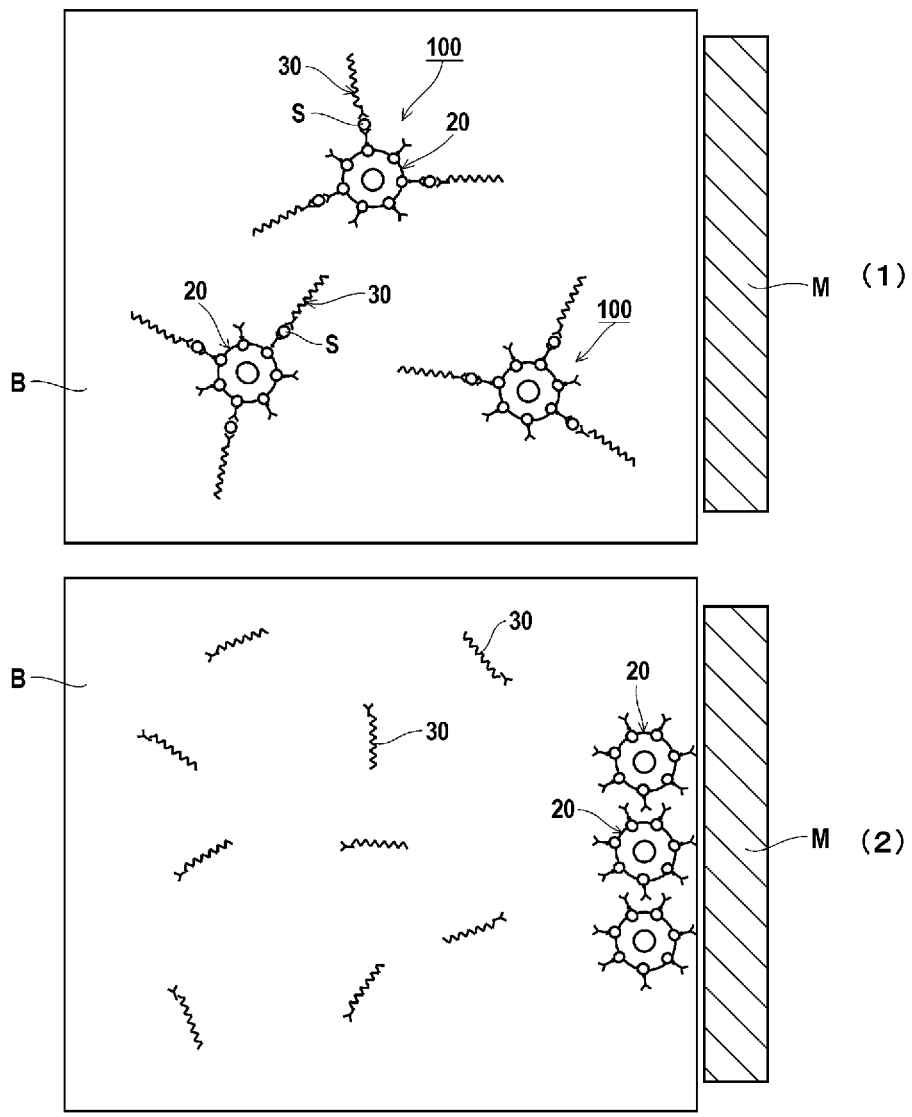
FIG. 1 is an explanatory drawing showing an example of a method of detecting a target substance according to the present invention.

FIG. 1 is an explanatory drawing showing an example of a method of detecting a target substance according to the present invention. In the detection method of the present embodiment, fluorescent labeling particles 20, dispersants 30, and analytes containing target substances S are mixed. Subsequently, presence or absence of dispersion of the thermoresponsive polymers is judged under conditions in which the thermoresponsive polymers are aggregated. At this time, the analytes are irradiated with the excitation light, and the dispersion is detected by the fluorescence emission.

Figure 5:
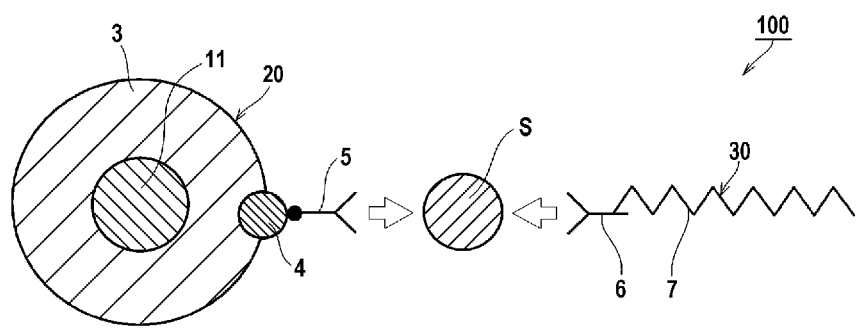
FIG. 5 is an explanatory view showing a state in which a fluorescent labeling particle forms a linked structure together with a target substance and a dispersant.

FIG. 1 (1) shows a case where the target substances S exist. At this time, as shown in FIG. 5 to be mentioned later, a linked structure 100 through the target substance S is formed, and dispersed without being aggregated in an analyte liquid. On the other hand, in a case where no target substance S exists (FIG. 1 (2)), any dispersant 30 and any fluorescent labeling particle 20 are not linked, and each of the fluorescent labeling particles 20 exists independently within a system. At this time, when the liquid is heated and the liquid temperature is adjusted to a critical solution temperature (CST) or higher, the fluorescent labeling particles 20 are aggregated. In the present embodiment, a magnet M is installed on a right side plane of a reaction vessel B. The fluorescent labeling particles 20 that are aggregated and strongly magnetized are attracted by magnetic force of this magnet, and gathered in the vicinity of the magnet M. On the other hand, when the state of FIG. 1 (1) in which the particles 20 exist in the form of the linked structures 100 having high dispersibility, aggregation of the fluorescent labeling particles 20 is not promoted, and the magnetism thereof is limited in a small state. Accordingly, even when the magnet M is placed laterally to the vessel B, the particles 20 are not attracted thereto, and a dispersion state is maintained.

In the present embodiment, the reaction liquid (vessel B) in which existence or non-existence of the target substances S is distinguished in the state of FIG. 1 described above is irradiated with the excitation light. Then, in FIG. 1 (1) in the state in which the target substances S is contained, fluorescence is limited to the emission from each of the fluorescent labeling particles 20, and is not intensified significantly, although somewhat emission is found in the liquid as a whole. On the other hand, in FIG. 1 (2) in which no target substance S is contained, when the liquid is irradiated with the excitation light, the fluorescent labeling particles 20 that are heated, and attracted in the vicinity of the magnet and in the aggregated state emit the fluorescence. The fluorescence results in the fluorescence emission of the fluorescent labeling particles 20 in the aggregated state and concentrated in a part, and the fluorescence can be detected in a significantly marked state.

That is, in the present embodiment, non-existence of the target substance is identified by development of the fluorescence emission of the labeling particles that are locally gathered in the above-described test liquid. To the contrary, existence of the target substance is identified by no development of the fluorescence emission of the above-described gathered particles.

Aggregation of the particles and accumulation thereof in the vicinity of the magnet are a phenomenon that occurs in conventional thermoresponsive magnetic particles in which the fluorescent material phase 2 is not used, according to which an orange-colored concentrated portion is observed, for example. However, the dispersion liquid in which no aggregation is caused is also slightly orange-colored, and when an amount of the target substance is small or the like, the color is not developed as a significantly distinct difference in several cases. In contrast, according to the present invention, the difference can be detected by the fluorescence, and therefore a marked change of the fluorescence emission can be detected. When the change is expressed by a difference in detection sensitivity (difference in absorbance or fluorescence intensity caused by existence or non-existence of the target substance), according to a preferred embodiment of the present invention, the difference can be improved by as much as 10 times to several hundred times in comparison with a conventional means. According to this effect, diagnosis that has been difficult by means of hitherto inspection equipment in a biochemistry field, for example in an infectious disease field can be achieved. However, the present invention shall not be limited and construed by exemplification of this improvement effect.

Further, in the present embodiment, the fluorescent material phase 2 that constitutes the fluorescent labeling particle 20 is formed of silica (continuous phase) 2a containing a fluorescent dye (dispersion layer) 2b. A detail thereof is mentioned later, but a silica raw material ordinarily has smaller specific gravity in comparison with a magnetic material, and becomes easily floatable in a medium of the analyte liquid, such as water. The effect is also produced, and a change of the dispersion and aggregation states becomes sharp, further leading to an improvement in the detection sensitivity.

In the present embodiment, presence or absence of dispersion (FIGS. 1 (1), 1 (2)) is judged by irradiation with the excitation light and detection of the fluorescence excited by the irradiation. From a viewpoint of detecting the fluorescence visually or with a general-purpose sensor, the above-described excitation light source preferably emits the excitation light in the following wavelength region. Examples of the excitation light source include a mercury lamp, a halogen lamp, and a xenon lamp. In the present invention, excitation light illuminated from a laser diode or light emitting diode is particularly preferably used. The detection system is preferably equipped with a filter for selectively transmitting light of specific wavelength from the excitation light source. Further, from the viewpoint of detecting only the fluorescence by visual observation or the like, it is more preferably equipped with a filter which is capable of removing the excitation light and transmitting only the fluorescence. In particular, the detection system preferably contains a photomultiplier tube or CCD detector capable of receiving the fluorescence. Accordingly, fluorescence with visually undeterminable intensity or wavelength can be detected, and further quantification of target substances can be made as its fluorescence intensity can be measured, enabling detection and quantification with high sensitivity.

The wavelength of the excitation light is preferably 300 nm or more, more preferably 400 nm or more, and particularly preferably 500 nm or more. The upper limit thereof is preferably 700 nm or less, more preferably 600 nm or less, and particularly preferably 550 nm or less. The fluorescence in the following range can be efficiently generated by adjusting the wavelength to the excitation light in this range, and such a case is preferable.

The wavelength of the fluorescence is preferably 350 nm or more, more preferably 450 nm or more, and particularly preferably 530 nm or more. The upper limit thereof is preferably 800 nm or less, more preferably 750 nm or less, and particularly preferably 580 nm or less. Detection by visual observation or with a generally used detector is facilitated by adjusting the wavelength in this range, and such a case is preferable.

In the following, the above-described fluorescent labeling particles that produce the excellent effects are described in more detail. In illustrated aspects, each material is schematically or exaggeratedly shown for ease of understanding, and the present invention shall not be limited and construed by the aspects shown in these figures.

In the detection method of the present invention, the test liquid containing the analyte is not particularly limited, but the liquid obtained by diluting the analyte with a buffer solution such as PBS is preferably used. Although a dilution factor is different depending on the analytes, the analyte can be diluted by 2 to 100 times, and used, for example. In addition thereto, an acid or a base for treatment may be appropriately incorporated into the test liquid. Although a concentration of a test substance in the test liquid is not particularly limited, the method of the present invention in which the detection sensitivity is high can be applied to the test liquid containing the test substance in 1 pg/mL or more, for example, and further preferably 1 ng/mL or more. An upper limit is not particularly provided, but is practically 1 mg/mL or less. More specifically, the upper limit can be set up by experiment for every item to be detected.

A concentration of the dispersant is not particularly limited, but is more preferably 0.01% by mass or more, and further preferably 0.1% by mass or more. An upper limit is not particularly provided, but is practically 5% by mass or less. A concentration of the labeling particles is not particularly limited, but is more preferably 0.01% by mass or more, and further preferably 0.1% by mass or more. An upper limit is not particular provided, but is practically 5% by mass or less.

A test temperature is not particularly limited, but the test is practically conducted at 25° C. or higher and 45° C. or lower.

The labeling particles related to the present embodiment preferably have properties of being aggregated immediately after heating. The target substance can be detected by utilizing the above properties. However, depending on a kind of the thermoresponsive polymer or a manner of providing the polymer onto the composite particles, response by heat needs time in several cases.

In taking into account such a matter also, with regard to detection of the fluorescence, measurement is preferably started after starting the above-described heating, and then a change of fluorescence intensity over time is preferably followed. High reproducibility and high sensitivity can be obtained by evaluating aggregation characteristics by using a differential between minimized fluorescence intensity at the time point of elapse of 600 seconds or more, and maximum fluorescence intensity obtained after starting the heating.

[Labeling Particles]

Figure 2:
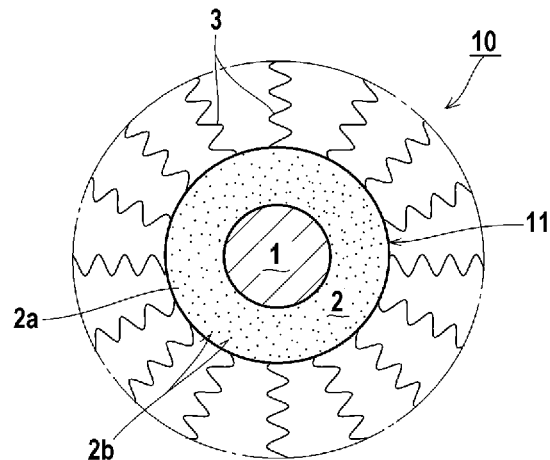
FIG. 2 is a side view schematically showing a thermoresponsive fluorescent particle constituting a labeling particle.

FIG. 2 is a side view schematically showing a thermoresponsive fluorescent particle 10 constituting a labeling particle as related to the present invention. In the present embodiment, a composite particle 11 has a form in which a transparent material phase (fluorescent silica phase) 2 forming a shell coats a surface of a magnetic material phase (magnetic material particle) 1 forming a core. Then, thermoresponsive polymers 3 are arranged on a surface of the composite particle 11. In the present embodiment, a core/shell-type composite particle is illustrated, but the present invention is not limited thereto. For example, the phases may be in a form into a sea-island form or in a state in which the phases are indefinitely mixed. However, even at this time, at least a part of the fluorescent material phase 2 is preferably exposed on the surface of the composite particle, and a greater part of the particle surface is more preferably constituted of the fluorescent material phase so that the fluorescence can be detected from outside. Accordingly, as the aspect of the sea-island form, the aspect is preferable in which the magnetic material phase constitutes an island portion, and the fluorescent material phase constitutes a sea portion. Specific examples of a similar aspect include a core-distributed particle inside which a number of cores formed by the above-described magnetic material phases exist.

The thermoresponsive polymers 3 are shown in the aspect in which the polymers 3 are radially extended from the surface of the composite particle 2 outward for convenience of illustration, but the present invention shall not be limited and construed by this aspect. Aspects related to adsorption of the polymer onto the surface are diversified, and generally indefinite. The polymers may have complicatedly entangled structure, or may be immobilized on the surface of the composite particle in the aspect of the particle form in which each molecule or several molecules are shrunk. However, the polymers are preferably in the state in which the excitation light at least partially reaches the composite particle, and the fluorescence emitted therefrom may reach the outside. In and after FIG. 3, the phases of this thermoresponsive polymers are simplified by hatching and shown.

Figure 3:
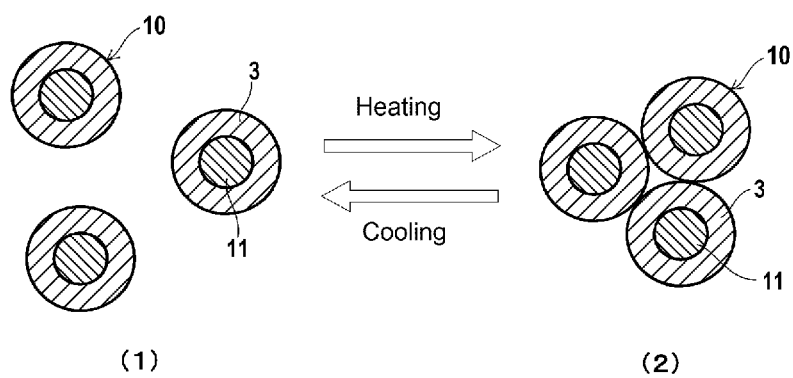
FIG. 3 is a side view schematically showing a change between aggregation and dispersion of thermoresponsive fluorescence particles by heating.

FIG. 3 is a side view schematically showing a change between aggregation and dispersion of thermoresponsive fluorescence particles 10 by heating. FIG. 3 (1) on a left-hand side in the figure shows a state before heating, in which the thermoresponsive fluorescence particles 10 are dispersed with each other in the system. In contrast, the particles 10 transition to an aggregated state by heating as in FIG. 3 (2) on a right-hand side. The reason why the change between aggregation and dispersibility is caused by heating as described above is not always clear. To describe the reason including presumption, it is considered that the polymers are shrunk by heating and approachable distances of adjacent composite particles become shorter, and therefore the aggregation is promoted. In the present embodiment, an example is shown in which the aggregation is promoted upon exceeding the critical solution temperature (CST) by heating, and dispersion is promoted below the critical solution temperature, but may be in a reverse manner. That is, an aspect may be formed in which the dispersion is promoted upon exceeding the critical solution temperature (CST), and the aggregation is promoted below the critical solution temperature.

Figure 4:
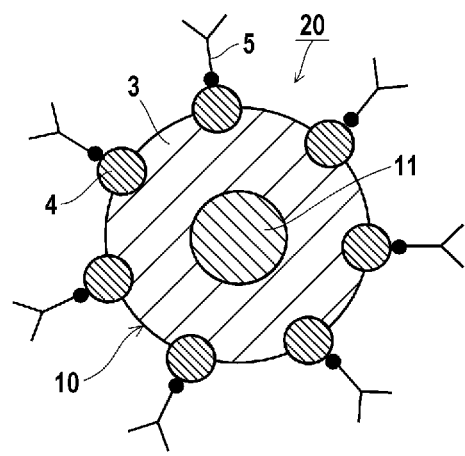
FIG. 4 is a side view schematically showing one embodiment of a fluorescent labeling particle.

FIG. 4 is a side view schematically showing one embodiment of a fluorescent labeling particle of the present invention. In the present embodiment, an example is shown in which linking materials 4 are provided on a surface of the composite particle 11, and binding substances 5 are immobilized therein. In an illustrated aspect, although the linking materials 4 are shown as when the linking materials 4 are arranged in an outside of the thermoresponsive polymer 3 (polymer leading end), which is only for convenience of illustration, and is not necessary to be in such an arrangement state. In actual fluorescent labeling particles, the thermoresponsive polymers 3 rather exist in an indefinite manner, and only need to arbitrarily exist in an entangled state or an adsorbed state therein, or the like. Conversely, when a material having a satisfactory molecular design is applied, the linking material may be introduced into the leading end of the thermoresponsive polymer as described above. As a modified aspect, the binding substances 5 may be introduced into the thermoresponsive polymer 3 without using the linking materials 4. Further, when the thermoresponsive polymer has properties of binding with the target substance, or the like, specific examples include fluorescent labeling particles in which no binding substance is used.

Herein, the binding substance 5 is referred to as a particle-side binding substance 5 in distinction from a dispersant-side binding substance 6 as mentioned later in several cases.

FIG. 5 is an explanatory view showing an example in which a fluorescent labeling particle 20 of the present invention forms a linked structure together with a target substance S. The particle-side binding substance 5 introduced into the fluorescent labeling particle has the properties of binding with the target substance S. On the other hand, in the present embodiment, a dispersant 30 is introduced into the system. The dispersant 30 is composed of a dispersant base 7 and a dispersant-side binding substance 6. This dispersant-side binding substance 6 also has the properties of binding with the target substance S. Accordingly, when the fluorescent labeling particle 20, the target substance S and the dispersant 30 coexist in the system, structure (linked structure 100) is formed in which the fluorescent labeling particle 20 and the dispersant 30 are linked through the target substance S. This linked structure 100 exhibits dispersibility in the system due to an effect of the dispersant 30 to prevent the fluorescent labeling particle 20 from being aggregated. Herein, FIG. 5 shows only one linking material 4 and one binding substance 5, but is simplified and preferably a large number thereof are provided typically as shown in FIG. 4.

The target substance S can be detected by utilizing the properties of binding of the dispersant 30 and the fluorescent labeling particles 20 with the target substance S, and the linked structure 100 as shown in FIG. 5, which is as shown in FIG. 1 described above.

[Composite Particle]
(Magnetic Material)

The magnetic material that can be used in the present invention is not particularly limited, but is preferably in a particle form. Specifically, the material has an average particle diameter of preferably 0.5 nm or more and less than 1,000 nm, and particularly preferably 3 nm or more and less than 200 nm. Specific examples of the magnetic materials (raw materials) include fine particles of magnetite, nickel oxide, ferrite, cobalt iron oxide, barium ferrite, carbon steel, tungsten steel, KS steel, a rare earth cobalt magnet and hematite.

(Fluorescent Material)

In the present invention, the phase containing the fluorescent material is preferably constituted of a continuous phase 2a formed of the transparent material and a dispersed phase 2b formed of the fluorescent material. In this case, the transparent material preferably contains silica or polystyrene.

Silica Phase

A method of forming the fluorescent silica phase as the above-described fluorescent material phase is not particularly limited, and the phase obtained by an arbitrary production method may be applied. Examples of the method include a sol-gel method described in Journal of Colloid and Interface Science, vol. 159, p. 150-157 (1993). In the present invention, a method of producing colloid silica particles containing fluorescent dye compounds as described in WO 2007/074722 A1 also serves as reference.

Specifically, an example in which a fluorescent dye as a fluorescent material is used is described. The silica phase containing a fluorescent dye can be prepared by reacting a fluorescent dye with a silane coupling agent and performing polycondensation of a product obtained through a covalent bond, ionic bond, or other chemical bonds or by adsorption with one or more of silane compounds to form a siloxane bond. Accordingly, the silica phase consisting of the organosiloxane component and the siloxane component that are bound to each other via siloxane bond are obtained. As one example, production can be made by reacting a fluorescent dye having or provided with an active group such as an N-hydroxysuccinimide (NHS) ester group, a maleimide group, an isocyanate group, an isothiocyanate group, an aldehyde group, a para-nitrophenyl group, a diethoxy methyl group, an epoxy group, and a cyano group with a silane coupling agent having a substituent which reacts with those active groups (e.g., an amino group, a hydroxy group, and a thiol group), and condensing and polymerizing the product obtained by forming a siloxane bond after forming a covalent bond with one or more types of silane compounds.

The following example relates to a case in which APS and tetraethoxy silane (TEOS) are used as a silane coupling agent and a silane compound, respectively.

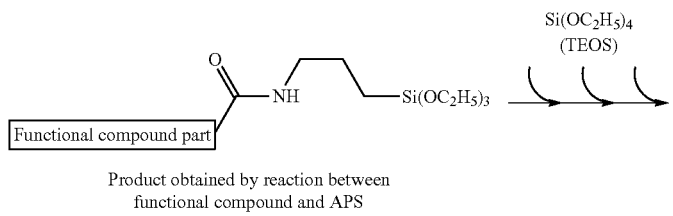

Product obtained by reaction between functional compound and APS

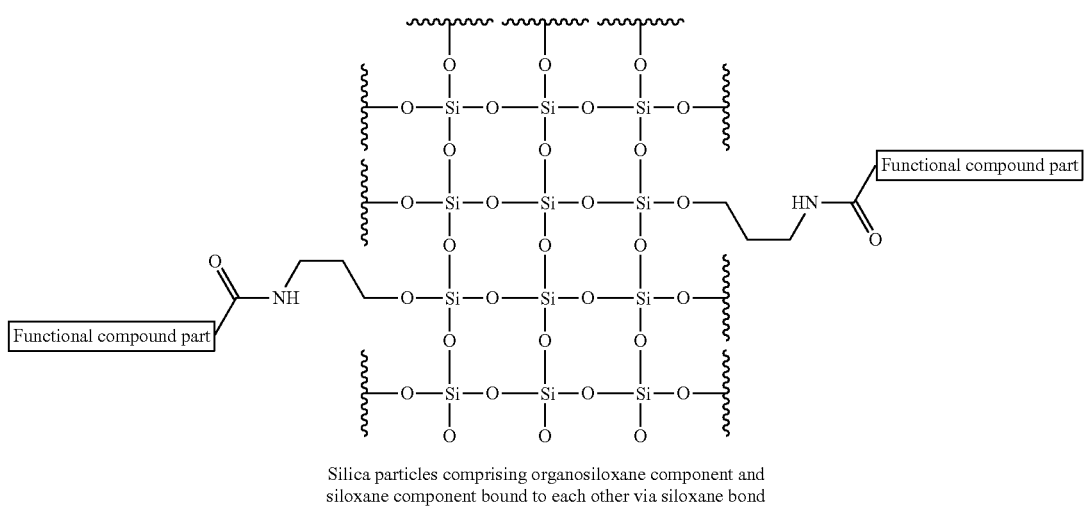

Silica particles comprising organosiloxane component and siloxane component bound to each other via siloxane bond Specific examples of the functional compound having or provided with an active group may include NHS ester group-containing fluorescence dye compounds such as 5-(and -6)-carboxytetramethylrhodamine-NHS ester (trade name, manufactured by emp Biotech GmbH), DY550-NHS ester or DY630-NHS ester represented as follows (each trade name, manufactured by Dyomics GmbH).

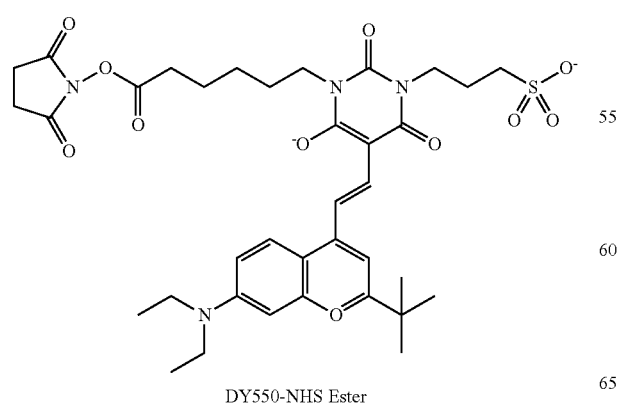

DY550-NHS Ester

-continued

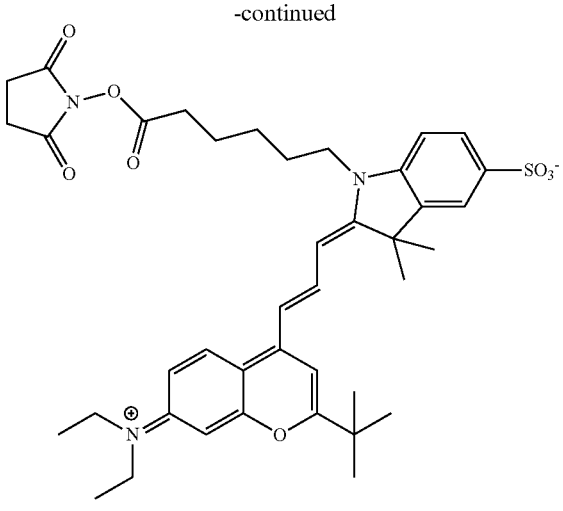

DY630-NHS Ester

Examples of the substituent-containing silane-coupling agent include an amino group-containing silane-coupling agent such as γ-aminopropyltriethoxysilane (APS), 3-[2-(2-aminoethylamino)ethylamino]-propyltriethoxysilane, N-2-(aminoethyl)-3-aminopropylmethyldimethoxysilane, and 3-aminopropyltrimethoxysilane. Among them, APS is preferable.

The silane compound to be condensed and polymerized is not particularly limited, and examples thereof include TEOS, γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, and 3-[2-(2-aminoethylamino)ethylamino]propyl-triethoxysilane. Among them, TEOS is preferable from the point of view of forming the siloxane component to be contained in the silica particles, and besides MPS and APS are preferable from the point of view of forming the organosiloxane component to be contained in the silica particles.

For example, spherical or almost spherical magnetic material/silica composite particles can be produced by using the above-described materials and providing the above-described magnetic particles into a reaction system so as to form a core. Meanwhile, the almost spherical particles mean particles having a major axis/minor axis ratio of 2 or less. For obtaining silica particles having a desirable average particle diameter, it is possible to remove particles having an excessively large particle diameter or an excessively small particle diameter by ultrafiltration by using an ultrafiltration membrane such as YM-10 or YM-100 (each trade name, manufactured by Millipore Corporation) or by recovering only a supernatant or precipitates after performing centrifugal separation with suitable acceleration of gravity.

The average particle diameter of the fluorescent composite particle is not specifically limited, but preferably 1 nm or more, and more preferably 20 nm or more. The upper limit thereof is preferably less than 1 μm, and more preferably 500 nm or less.

In the present invention, the average particle diameter is an average diameter of the circle (average circle-equivalent diameter) obtained by measuring the total projected area of 100 pieces of randomly-selected labeling reagent silica particles for example in an image obtained under transmission electron microscope (TEM) or scanning electron microscope (SEM) using an image processing equipment, dividing the total area with the number of the labeling reagent silica particles (100 pieces), and determining the circle having an area equivalent to that.

Further, the "average particle diameter" indicates an average particle diameter of particles consisting of only primary particles, which is different from the "particle size according to a dynamic light scattering method" described below having a concept including secondary particles formed by aggregation of primary particles.

As described herein, the "particle size according to the dynamic light scattering method" is measured by the dynamic light scattering method, and it is a concept including secondary particles formed by aggregation of primary particles as well as primary particles, different from average particle diameter. This particle size is an indicator for evaluating dispersion stability of the complex particles described above.

Examples of a device for measuring the particle size according to the dynamic light scattering method include Zetasizer Nano (trade name, manufactured by Malvern Instruments Ltd.). According to the method, fluctuation in light scattering intensity over time that is caused by light scatterers such as fine particles is measured, the speed of the light scatterers in Brownian motion is calculated based on an autocorrelation function, and the particle size distribution of the light scatterers is determined based on the results.

The fluorescent silica particles preferably have monodispersion as a granular substance. The variation coefficient, so-called CV value, of the particle size distribution is not specifically limited, but preferably 10% or less, and more preferably 8% or less.

Latex Phase

In the present invention, it is preferable to use the above-described silica fine particles because the effect thereof is significant, but in addition thereto or in place thereof, a latex phase may be used as the continuous phase of the fluorescent material phase in the composite particles. Examples of the material for constituting the latex phase include synthetic polymer particles consisting of polystyrene, styrene-sulfonic acid (salt) copolymer, styrene-methacrylic acid copolymer, acrylonitrile-butadiene-sulfonic acid copolymer, vinyl chloride-acrylic acid ester copolymer, or vinyl acetate-acrylic acid ester copolymer. Further, as for the method of introducing a dye into the latex phase, methods disclosed in JP-A-2000-178309 ("JP-A" means unexamined published Japanese patent application), JP-A-10-48215, JP-A-8-269207, JP-A-6-306108, or the like can be used. Immobilization of a fluorescent substance (labeling substance) for those kinds of particles can be suitably performed according to a common method. For example, reference can be made to Japanese JP-T-2005-534907 ("JP-T" means published searched patent publication), JP-A-2010-156642 and JP-A-2010-156640, or the like.

An amount of the fluorescent material (fluorescent dye) in the phase of the fluorescent material is not particularly limited in the present invention, but is preferably 0.05 part by mass or more, and more preferably 0.10 part by mass or more when the amount of the transparent material (continuous phase) is taken as 100 parts by mass. An upper limit is preferably 1.0 part by mass or less, and more preferably 0.50 part by mass or less. A ratio of the phase of the magnetic material to the phase of the fluorescent material may also be appropriately adjusted.

At the ratio of the phase of the magnetic material to the phase of the transparent material, the fluorescence particles are preferably gathered due to action of the phase of the magnetic material in a predetermined portion for detection. On the other hand, in the phase of the transparent material, the fluorescent material preferably exists in the transparent material at a specific proportion to allow effective measurement of fluorescence. Accordingly, the ratio of the phase of the transparent material to the phase of the fluorescent material, and the ratio of the phase of the magnetic material to the phase of the transparent material are preferably designed so as to satisfy the above-described purposes.

Moreover, the ratio of the phase of the magnetic material to the phase of the fluorescent material can be determined from the ratio of the phase of the transparent material to the phase of the fluorescent material, and the ratio of the phase of the magnetic material to the phase of the transparent material.

(Thermoresponsive Polymer)

The thermoresponsive polymer preferably causes no structural change, even if the polymer is bounded with a molecule having an electric charge. As the thermoresponsive polymer, a polymer having the critical solution temperature (hereinafter, also referred to as CST) is preferable. This critical solution temperature (CST) means a temperature serving as a border at which characteristics or morphologies of the polymer are changed. The thermoresponsive polymer may be a polymer exhibiting a lower critical solution temperature (LCST) or an upper critical solution temperature (UCST). When the thermoresponsive polymer exhibits the lower critical solution temperature (LCST), specific examples include a polymer that causes aggregation when the liquid temperature is increased, and redispersion when the temperature is decreased. Conversely, when the thermoresponsive polymer exhibits the upper critical solution temperature (UCST), specific examples include a polymer that causes aggregation when the liquid temperature is decreased, and redispersion when the temperature is increased. The critical solution temperature (CST) is preferably 10° C. or higher, and more preferably 30° C. or higher. An upper limit is preferably 100° C. or lower, and more preferably 50° C. or lower.

Herein, the lower critical solution temperature and the upper critical solution temperature can be determined as described below, for example. First, a sample is placed in a cell of an absorptiometer and heated at a rate of 1° C./min. During heating, a change of transmittance at 550 nm is recorded. Here, the transmittance when the polymer is melted in a transparent state is taken as 100% and the transmittance when the polymer is completely aggregated is taken as 0%. Then, a temperature at which the transmittance becomes 50% is determined as LCST.

Specific examples of the polymer having the lower critical solution temperature include polymers composed of N-substituted (meth)acrylamide derivatives such as N-n-propylacrylamide, N-isopropylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine and N-methacryloylmorpholine; polyoxyethylene alkylamine derivatives such as hydroxypropylcellulose, a polyvinyl alcohol partially acetylated product, polyvinyl methyl ether, a (polyoxyethylene-polyoxypropylene) block copolymer and polyoxyethylene lauryl amine; polyoxyethylene sorbitan ester derivatives such as polyoxyethylene sorbitan laurate; (polyoxyethylene alkylphenyl ether)(meth)acrylates such as (polyoxyethylene nonylphenyl ether) acrylate and (polyoxyethylene octylphenyl ether) methacrylate; and polyoxyethylene (meth)acrylic acid ester derivatives of (polyoxyethylene alkyl ether)(meth)acrylates, such as (polyoxyethylene lauryl ether)acrylate and (polyoxyethylene oleyl ether)methacrylate. Further, a polymer thereof or a copolymer formed of at least two kinds of monomers thereof can also be used. Moreover, a copolymer of N-isopropylacrylamide and N-t-butyl acrylamide can also be used. When the polymer containing the (meth)acrylamide derivative is used, any other copolymerizable monomer may be copolymerized with this polymer in the range in which the resultant copolymer has the lower critical solution temperature.

Among them, a polymer composed of at least one kind of monomers selected from the group consisting of N-n-propylacrylamide, N-isopropylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine and N-methacryloylmorpholine, or a copolymer of N-isopropylacrylamide and N-t-butylacrylamide can be preferably used.

As the polymer having the upper critical solution temperature, a polymer formed of at least one kind of monomer selected from the group consisting of acroylglycinamide, acroylnipecotamide, acryloylasparaginamide, acryloyl glutaminamide and the like can be used. Moreover, the polymer may be a copolymer formed of at least two kinds of these monomers. With these polymers, any other copolymerizable monomer such as acrylamide, acetylacrylamide, biothionol acrylate, N-bithionyl-N'-methacroyltrimethylene amide, acroylsarcosine amide, methacrylicsarcosine amide and acroylmethyluracil may be copolymerized in the range in which the resultant copolymer has the upper critical solution temperature.

As the thermoresponsive polymer, a polymer described in Japanese Patent No. 4518767, for example can be preferably used.

(Immobilization of Thermoresponsive Polymer onto Composite Particle)

The thermoresponsive polymer can be immobilized thereonto through polyhydric alcohol or a polyhydric alcohol derivative. This thermoresponsive polymer may be immobilized thereonto by being subjected to graft polymerization with the polyhydric alcohol or the polyhydric alcohol derivative immobilized on the surface of the composite particle, or by binding a functional group in a terminal or a side chain of the polymer with a functional group of the polyhydric alcohol or the polyhydric alcohol derivative. An average particle diameter of the composite particle on which the thermoresponsive polymer is immobilized (thermoresponsive fluorescent particle) becomes larger by a portion of the thermoresponsive polymer in comparison with the above-described composite particle, but a preferred range thereof is substantially similar to the range specified as the composite particle.

The polyhydric alcohol preferably has at least two hydroxy groups in a constitutional unit. Specific examples include dextran, polyvinyl alcohol, mannitol and sorbitol. Moreover, a compound that has an epoxy group and forms a polyhydric alcohol structure after ring opening, such as a glycidyl methacrylate polymer, can also be used. As the polyhydric alcohol derivative, polyhydric alcohol into which a reactive functional group or polymerizable group, such as carboxyl, amino, epoxy, thiol, methacrylic or acrylic is introduced by modification can be used.

(Linking Material)

The linking material is an arbitrary material, and is preferably selected and used appropriately when such a material is necessary for introduction of the binding substance. A kind thereof is not particularly limited, but a material that can be incorporated into the thermoresponsive polymer and has the properties of binding with the binding substance is preferable. In taking into account use of a biological substance in the binding substance, specific examples include biotin, avidin, streptoavidin, a primary antibody and a secondary antibody.

As a method of incorporating the linking material into the thermoresponsive polymer, the description in WO 01/09141 or Japanese Patent No. 4518767 can serve as reference. Specifically, biotin or the like is bound with a polymerizable functional group such as a methacrylic group and an acrylic group into an addition-polymerizable monomer, and the monomer is copolymerized with any other monomer to perform incorporation. As an alternative method, such a method can be utilized, in which a monomer having a functional group such as carboxylic acid, an amino group or an epoxy group is copolymerized with any other monomer during polymerization of a polymer to bind an antibody-affinity substance (for example, melon gel, protein A, protein G) with the polymer through this functional group according to an ordinary method. Alternatively, a monomer having a functional group such as carboxylic acid, an amino group or an epoxy group may be copolymerized with any other monomer during polymerization of a polymer to directly bind an antibody (binding substance) against an antigen of a detection object with these functional groups according to an ordinary method. Thus, use of the linking substance can be omitted.

(Particle-side Binding Substance)

The particle-side binding substance is an arbitrary material, and only needs to be appropriately selected when necessary according to a kind of target substance. As a biomolecule (binding substance) to be combined or absorbed on the surface of the composite particle, there includes antigens, antibodies, DNAs, RNAs, sugars, polysaccharides, ligands, receptors, proteins, peptides and the like. Here, the term "ligand" means a substance capable of specifically binding to a protein, and examples thereof include substrates capable of binding to enzyme, coenzymes, regulatory factors, hormones, neurotransmitters, and the like. Thus, the ligands include low-molecular weight molecules or ions as well as high-molecular weight substances. The antibody used herein may be any type of immunoglobulin molecules, or immunoglobulin molecule fragments having an antigen binding site, such as Fab. Moreover, the antibody may be a monoclonal antibody or a polyclonal antibody, but is preferably two kinds of monoclonal antibodies having different antigen recognition sites. A technique for binding the binding substance with the linking substance is not particularly limited, and binding can be performed by an ordinary method in this kind of technologies.

Preferred materials are shown in Table A below in conformity with an example shown in FIG. 5.

TABLE A

| Labeling particle | Magnetic material | Magnetite, Nickel oxide, Ferrite or the like |
|---|---|---|
| | Fluorescent material (dye) | 5- (and -6)-carboxytetramethylrhodamine-NHS ester DY550-NHS ester and the like |
| | Transparent material | Silica, Latex (polystyrene) |
| | Linking material | Streptavidin |
| | Binding substance | Biotin-introduced antibody |
| Target substance | | TSH antigen |
| Dispersant | Dispersant base | Polyacrylic acid |
| | Dispersant-side binding substance | Antibody |

[Dispersant]
(Dispersant Base)

The dispersant base is a hydrophilic high molecular weight compound, for example, and is preferably a polyanion or a polycation. The polyanion means a substance having a plurality of anion groups, and the polycation means a substance having a plurality of cation groups. Specific examples of the polyanion include nucleic acid such as DNA and RNA. These nucleic acids have properties of the polyanion due to existence of plural pieces of phosphodiester groups along a skeleton of the nucleic acid. Moreover, the polyanion includes polypeptide containing a large number of carboxylic acid functional groups (polypeptide composed of amino acid such as glutamic acid and aspartic acid), polyacrylic acid, polymethacrylic acid, a polymer containing, as a polymerization component, acrylic acid and methacrylic acid, and a polysaccharide such as carboxymethylcellulose, hyaluronic acid and heparin. On the other hand, specific examples of the polycation include polylysine, polyarginine, polyornithine, polyalkylamine, polyethyleneimine and polypropyleneimine. In addition, the number of functional groups in the polyanion (carboxyl group) or the polycation (amino group) is preferably 25 or more.

(Dispersant-side Binding Substance)

The dispersant-side binding substance only needs to be appropriately selected when necessary according to the kind of target substance. A kind thereof is preferably selected in taking into account introduction into the dispersant base. Specific examples are identical with the substances exemplified as the above-described particle-side binding substance.

The method of binding the binding substance with the dispersant base is not particularly limited, and specific examples include a method in which mutual affinity substances (for example, avidin and biotin, glutathione and glutathione S transferase) are bound to both to indirectly bind the dispersant base and the binding substance through these substances. When both are directly bound, both may be bound through a functional group. When such a functional group is used, for example, both can be bound according to maleimide-thiol coupling in the method of Ghosh, et al (Ghosh et al: Bioconjugate Chem., 1, 71-76, 1990). Specific examples include two methods described below. In a first method thereof, while a mercapto group (alias, a sulfhydryl group) is introduced first into a 5' terminus of nucleic acid, a maleimide group is introduced into an antibody by allowing 6-maleimide hexanoic acid succinimide ester (for example, "EMCS (trade name)" (manufactured by Dojindo Laboratories)) to react with the antibody. Next, two kinds of these substances are bound through the mercapto group and the maleimide group. In a second method, a mercapto group is introduced first into a 5' terminus of nucleic acid in a manner similar to the first method, and a maleimide group is further introduced into a 5' terminus of nucleic acid by allowing N,N-1,2-phenylenedimaleimide being a homo bifunctional reagent to react with this mercapto group. Meanwhile, a mercapto group is introduced into an antigen. Next, two kinds of these substances are bound through the mercapto group and the maleimide group.

In addition thereto, as a method of introducing nucleic acid into protein, for example, methods described in Nucleic Acids Research, Vol. 15, p. 5275 (1987), and Nucleic Acids Research, Vol. 16, p. 3671 (1988) are known. These technologies can be applied to binding of the antibody with the nucleic acid.

[Target Substance]

As the target substance, a substance used in clinical diagnosis is exemplified, and specific examples include, as contained in body fluid, urine, sputum, feces and the like, human immunoglobulin G, human immunoglobulin M, human immunoglobulin A, human immunoglobulin E, human albumin, human fibrinogen (fibrin and a decomposition product thereof), α-fetoprotein (AFP), C-reactive protein (CRP), myoglobin, a carcinoembryonic antigen, a hepatitis virus antigen, human chorionic gonadotropin (hCG), human placental lactogen (HPL), an HIV virus antigen, allergen, bacteriotoxin, a bacteria antigen, an enzyme, hormone (for example, human thyroid stimulating hormone (TSH), insulin and the like) and a medical agent.

EXAMPLES

The present invention will be described in more detail based on Examples given below, but the invention is not limited to that.

A system shown in FIG. 5 was reproduced using materials shown in Table A. The labeling particles were particles in which magnetic particles were coated with silica particles as shown in Table A, and an average particle diameter thereof was about 200 nm. The particles were incorporated into a test liquid containing analytes, and the resultant material was heated at about 50° C. for 15 minutes. Then, the resultant material was irradiated with excitation light (550 nm), and a target substance contained in the above-described analytes was detected depending on a state of light emission (580 nm) of the above-described labeling particles. At this time, it was confirmed that, under existence of the analyte, dispersion was maintained because a dispersant was bound with magnetic fluorescent thermoresponsive particles through the target substance, resulting in causing no change in fluorescence intensity in comparison with the intensity before heating. To the contrary, under non-existence of the analyte, the magnetic fluorescent thermoresponsive particles were aggregated by heating and then precipitated, resulting in causing reduction of the fluorescence intensity in composition with the intensity before heating.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Magnetic material phase (magnetic material particle, core)
2 Transparent material phase (fluorescent silica phase, shell)
  2a Transparent material (continuous phase)
  2b Fluorescent material (fluorescent dye, dispersion phase)
3 Thermoresponsive polymer (thermoresponsive polymer phase)
4 Linking material
5 Particle-side binding substance
6 Dispersant-side binding substance
7 Dispersant base
10 Thermoresponsive fluorescence particle
11 Composite particle
20 Fluorescent labeling particle (magnetic fluorescent thermoresponsive particle)
30 Dispersant
100 Linked structure
S Target substance
M Magnet

The invention claimed is:

1. A method of detecting a target substance in a sample, comprising the steps of:
  mixing the sample, a plurality of labeling particles and a dispersant to prepare a test liquid, wherein the labeling particle comprises a composite particle, a thermoresponsive polymer on the surface of the composite particle, and a biomolecule having properties of binding with the target substance, wherein the composite particle comprises a phase having a magnetic material and a phase having a fluorescent material, wherein the phase having the fluorescent material is constituted of a continuous phase formed of a transparent material and a dispersed phase formed of the fluorescent material;
  heating the test liquid, wherein an aggregation state of the labeling particles is changed by the heating step, wherein the target substance, the dispersant and the labeling particles are linked to form a linked structure that is dispersed without being aggregated when the target substance present in the sample, and wherein the labeling particles are aggregated by heating when the target substance does not present in the sample;
  applying a magnetic force to the test liquid, whereby the labeling particles in an aggregated state are gathered in a portion provided with the magnetic force;
  irradiating the test liquid with excitation light; and
  detecting the presence or absence of the target substance in the sample depending on a state of light emission of the aggregated labeling particles gathered in a portion provided with the magnetic force.

2. The method of detecting the target substance according to claim 1, wherein a wavelength of the excitation light is 300 to 700 nm and a wavelength of the fluorescence is 350 to 800 nm.

3. The method of detecting the target substance according to claim 1, wherein the test liquid is heated so as to span a critical solution temperature (CST) of the thermoresponsive polymer in the range of 10° C. to 100° C.

4. The method of detecting the target substance according to claim 1, wherein an average particle diameter of the composite particle is less than 1 μm.

5. The method of detecting the target substance according to claim 1, wherein the transparent material comprises silica or polystyrene.

6. The method of detecting the target substance according to claim 1, wherein the magnetic material is magnetite, nickel oxide, ferrite, cobalt iron oxide, barium ferrite, carbon steel, tungsten steel, KS steel, a rare earth cobalt magnet or hematite.

* * * * *